United States Patent
Mezger et al.

[11] Patent Number: 6,096,265
[45] Date of Patent: Aug. 1, 2000

[54] PROCESS FOR VAPORIZING HYDROGEN PEROXIDE TO STERILIZE SURFACES

[75] Inventors: Ulrich Mezger, Corseaux; Christian Schmied, Ursellen, both of Switzerland

[73] Assignee: Nestec SA, Vevey, Switzerland

[21] Appl. No.: 08/700,659

[22] Filed: Aug. 9, 1996

[30] Foreign Application Priority Data

Aug. 11, 1995 [EP] European Pat. Off. .............. 95202189

[51] Int. Cl.[7] ....................................................... A61L 2/00
[52] U.S. Cl. ................................ 422/28; 422/29; 422/33; 422/108
[58] Field of Search ...................... 422/28, 27, 29, 422/32, 292, 298, 299, 9, 302, 306, 33, 108; 261/161, 99; 239/145

[56] References Cited

U.S. PATENT DOCUMENTS

| | | | |
|---|---|---|---|
| 3,583,635 | 6/1971 | Lemelson | 239/145 |
| 4,511,538 | 4/1985 | Buchner et al. | 422/303 |
| 4,683,701 | 8/1987 | Rangawala et al. | 53/167 |
| 4,742,667 | 5/1988 | Müller et al. | 53/167 |
| 4,743,407 | 5/1988 | Apel | 261/99 |
| 5,038,742 | 8/1991 | Uddin | 123/549 |
| 5,178,841 | 1/1993 | Vokins et al. | 422/298 |
| 5,258,162 | 11/1993 | Andersson | 422/28 |
| 5,997,827 | 12/1999 | Mezger | 422/292 |

FOREIGN PATENT DOCUMENTS

0481361A1 of 1992 European Pat. Off. .
1582060 of 1980 United Kingdom .

*Primary Examiner*—Yvonne Eyler
*Assistant Examiner*—Eliane Lazar-Wesley
*Attorney, Agent, or Firm*—Vogt & O'Donnell, LLP

[57] ABSTRACT

For sterilizing surfaces with hydrogen peroxide, a stream of hot air is fed through a tube which includes a porous section, and vaporized hydrogen peroxide is diffused from the porous section into the hot air stream to obtain a combined hot air and vaporized stream mixture for supplying the vaporized hydrogen peroxide to a surface for sterilizing the surface. Further for carrying out the process, liquid hydrogen peroxide is fed to the porous section for forming a film on the porous section, and the porous section is heated to a temperature to vaporize the hydrogen peroxide for diffusion via the porous section into the hot air stream.

16 Claims, 2 Drawing Sheets

PROCESS FOR VAPORIZING HYDROGEN PEROXIDE TO STERILIZE SURFACES

BACKGROUND OF THE INVENTION

This invention concerns a process for continuously sterilising surfaces in an aseptic filling line with a mixture of air and gaseous hydrogen peroxide, wherein a stream of hot air is fed through a feeding tube to the different surfaces to be sterilised.

The sterilisation of packaging materials with gaseous hydrogen peroxide is well known in the art. The European Patent Application Publication No. 0 481 361 concerns an apparatus for sterilising containers which comprises a nozzle as the source of liquid hydrogen peroxide and heated air for vaporising said hydrogen peroxide. The drawback of this system is that the use of a nozzle for introducing the liquid hydrogen peroxide leads to a tendency for blocking said nozzle, and secondly, it is more difficult to enable uniform atomisation and a complete vaporisation when droplets have to be vaporised. Furthermore, specific vaporisation chambers often require a high vaporisation temperature and the decomposition rate of hydrogen peroxide can be relatively high. Finally, the apparatus of the above mentioned patent application is complicated, which makes the maintenance and cleaning more difficult and expensive.

SUMMARY OF THE INVENTION

The aim of the present invention is to overcome the above-mentioned drawbacks and particularly to find a process, wherein a complete vaporisation of the aqueous hydrogen peroxide, a constant concentration of hydrogen peroxide in the vapour-phase and a minimised decomposition of hydrogen peroxide can be guaranteed.

This invention concerns a process for continuously sterilizing surfaces with a mixture of air and gaseous hydrogen peroxide wherein a stream of hot air is fed through a feeding tube to the surface to be sterilised, characterised in that the hot air is mixed with completely vaporised hydrogen peroxide, wherein the vaporised hydrogen peroxide is diffused from a porous section of said feeding tube into the hot air stream to obtain a combined hot air and vaporised hydrogen peroxide mixture for supplying the vaporised hydrogen peroxide to a surface for sterilising the surface said vaporized hydrogen peroxide being obtained by forming a thin film of liquid hydrogen peroxide in a porous tube and by heating it, said porous tube forming part of the hot air feeding tube and diffusing said vaporized hydrogen peroxide into the hot air stream.

The process according to the present invention takes advantage of the fact that heat and mass transfer during evaporation are considerably higher when a thin film of liquid is in contact with a hot surface, compared to the above-mentioned European '361 Application technology with evaporation of droplets in a hot air stream. Therefore, the formation of a well-spread thin film of liquid hydrogen peroxide is ensured by using a porous tube.

DETAILED DESCRIPTION OF THE INVENTION

According to the present invention, "under surfaces" is to be understood as any type of enclosures, such as packagings made with any type of packaging material, such as glass, plastic, or metal.

The normal temperature of vaporisation of hydrogen peroxide in aqueous phase is about 107° C. with approximately 35% hydrogen peroxide in weight: the vaporisation of the hydrogen peroxide is performed at a temperature of 110 to 130° C. of the heating equipment. The temperature must be high enough to guarantee the vaporisation of all the hydrogen peroxide, but not too high to avoid a decomposition of said $H_2O_2$. Typically, the temperature of heating equipment is around 120° C.

The process according to the invention is continuous and taking in account the new way of vaporisation, the consumption of hydrogen peroxide can be reduced. The concentration of hydrogen peroxide is from 5 to 20 mg/liter of air.

To prevent the gaseous hydrogen peroxide from condensing, the whole apparatus is kept at a temperature of the order of 120° C. The hot air stream is generated by means of a low pressure ventilator and a simple heat exchanger and can be easily monitored using a flow meter.

After the sterilisation step, according to the concentration of the hydrogen peroxide, condensation of said hydrogen peroxide can occur, and in this case, it is preferred to remove these residues and to have a drying air flow arriving on the sterilised surfaces at a temperature of the order of 120° C.

It is also preferable according to the invention to be sure that an efficient sterilisation effect can be guaranteed, and it is therefore preferable to have means for monitoring the temperature, the hot air flow rate and the hydrogen peroxide concentration of the gaseous mixture. The hot air flow rate depends on the diameter of the feeding tube and on the number of containers which has to be sterilised on the line. Normally, the air rate is from 20 to 50 l/min per container. Concerning the hydrogen peroxide concentration, it is measured on-line by means of a photometer or a system based on the thermal effect of a catalytic decomposition of hydrogen peroxide, wherein a small part of the stream of hydrogen peroxide is sucked through the measuring device (photometer or catalyst) using a small vacuum pump, which is explained in more detail hereunder. The invention concerns further an apparatus for continuously sterilising containers in an aseptic filling line, wherein the apparatus comprises a feeding tube for feeding a mixture of hot air and vaporised hydrogen peroxide and a plurality of nozzles through which said mixture is introduced on the surfaces to be sterilised, wherein the feeding tube includes a section formed by a porous tube for feeding directly the gaseous hydrogen peroxide into the stream of hot air, said tube being surrounded by a heated means.

As already said before, it is preferred that the hydrogen peroxide is totally vaporized at the moment of mixing with the hot air.

The porous tube is a sintered metal tube, for example made from stainless steel having pores of a diameter of 20 to 80 microns, preferably on the order of 40 microns. If the pore size is below 20 microns, large pumping pressures are required for the liquid hydrogen peroxide and the pores run the risk of becoming blocked. On the contrary, if the pore size is too great, this leads to the risk that not all the hydrogen peroxide is vaporised.

The thickness of the porous tube should be selected carefully for best results. In thin tubes, the contact period is not sufficient for allowing vaporisation and in tubes which are too thick, too great a decomposition of the hydrogen peroxide can occur. The best thickness is from 3 to 4 mm. Concerning the length, it must be sufficient to allow an adequate flow rate and evaporation of the hydrogen peroxide, leading to an efficient concentration in the stream of hot air, the optimal length being 15 to 30 cm.

The liquid hydrogen peroxide is in aqueous solution. The concentration is not critical, but is preferably between 5 and 45%, preferably about 35%. As already mentioned above, it is preferred to prevent any possibility of condensation, for example of steam coming from the water of the hydrogen peroxide, and the feeding tube is therefore steam heated at a temperature to about 120° C.

In the case of an apparatus, which could be operated under ultrahygienic conditions, it would be also possible to reduce the hydrogen peroxide to as low as 0; the sterilization efficiency is reduced to vegetative germs only compared with a reduction of the thermophilic spores for hydrogen peroxide, and it necessitates a heating of the feeding tube as high as 170° C.

In the device according to the invention, the feeding of the gaseous hydrogen peroxide occurs through one feeding inlet or several, depending on the machine capacity. The diameter of the feeding tube of hot air is correspondingly increased.

To measure the hydrogen peroxide concentration, the apparatus comprises further a photometer or a system based on the catalytic decomposition of hydrogen peroxide.

Hydrogen peroxide shows a characteristic absorption peak at a wavelength of 200 nm. A standard photometer is combined with a vacuum pump, which guarantees a constant flow of the test gas through the measuring cell. To keep the test gas above the dew point, cylindrical and heated measuring cells are used.

The thermal effect of the catalytic decomposition of hydrogen peroxide can easily be measured by means of a small catalyst. A constant small part of the gas flows through a little catalyst that consists of a ceramic wafer material that is kept at a temperature of 120° C. Due to the exothermic decomposition of the gaseous hydrogen peroxide into oxygen and water, a significant temperature increase of the test gas can be measured between the inlet and the outlet of the catalyst. This temperature increase can be exactly correlated with the hydrogen peroxide concentration.

The apparatus according to the invention gives a tubular distribution system for the $H_2O_2$ vapour, without any valve, orifices or other components, built in. The correct gas distribution to the individual surfaces is assured by exchangeable nozzles, which can be calibrated at the corresponding outlets, to ensure amount of gas wanted at the specific place.

Both these control systems are appropriate for the continuous monitoring of the hydrogen peroxide vaporisation quality and the sterilisation effect during production.

An embodiment of the invention is described with reference to the accompanying drawings.

BRIEF DESCRIPTION OF THE DRAWING FIGURES

DETAILED DESCRIPTION OF THE DRAWING FIGURES

Figure 1:
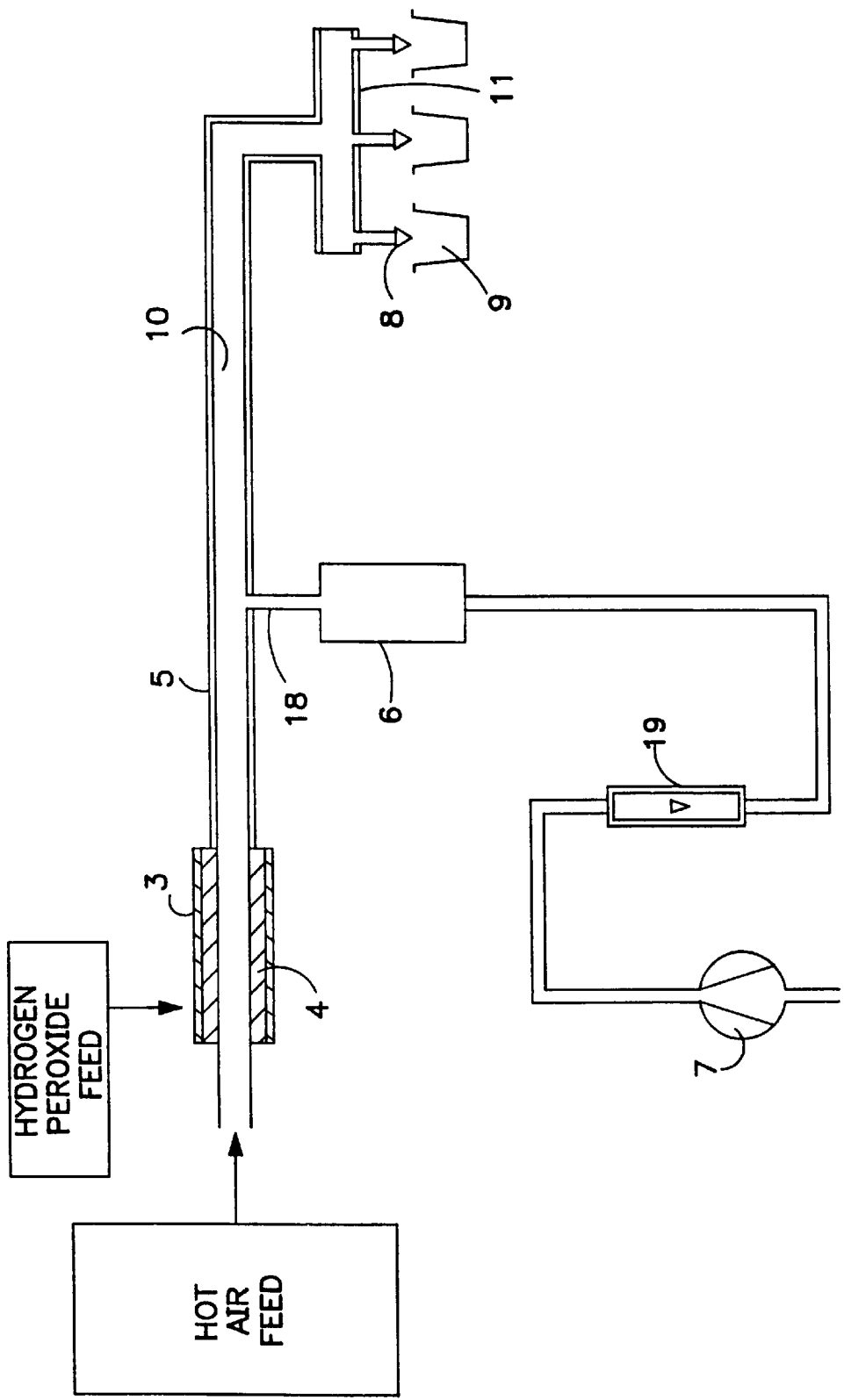
FIG. 1 shows a schematic view of the apparatus according to the invention.

FIG. 1 demonstrates the principle of a package sterilisation by means of the hydrogen peroxide vaporiser. The liquid hydrogen peroxide, is fed directly onto the porous tube (4) by means of a positive pump (not shown), said peroxide being vaporised by means of the steam jacket (3) heating the porous tube. The hot air stream, is generated by means of a conventional low pressure system (not shown). To prevent the gaseous hydrogen peroxide and the steam from condensation, the feeding tube (10) is heated with a steam jacket (5). The packages (9) to be sterilised are disposed directly under the corresponding nozzles (8) diffusing the mixture of hot air and gaseous hydrogen peroxide. A measuring device (6), such as a photometer, is disposed on-line via piping (18), as illustrated, to control the concentration of the hydrogen peroxide in the line, a measured part controlled by a flow meter (19) of the main stream being sucked through said measuring device with the help of a small vacuum pump (7). The nozzles (8) are also equipped with a steam jacket (11), avoiding therefore any risk of condensation in the whole sterilising apparatus.

Figure 2:
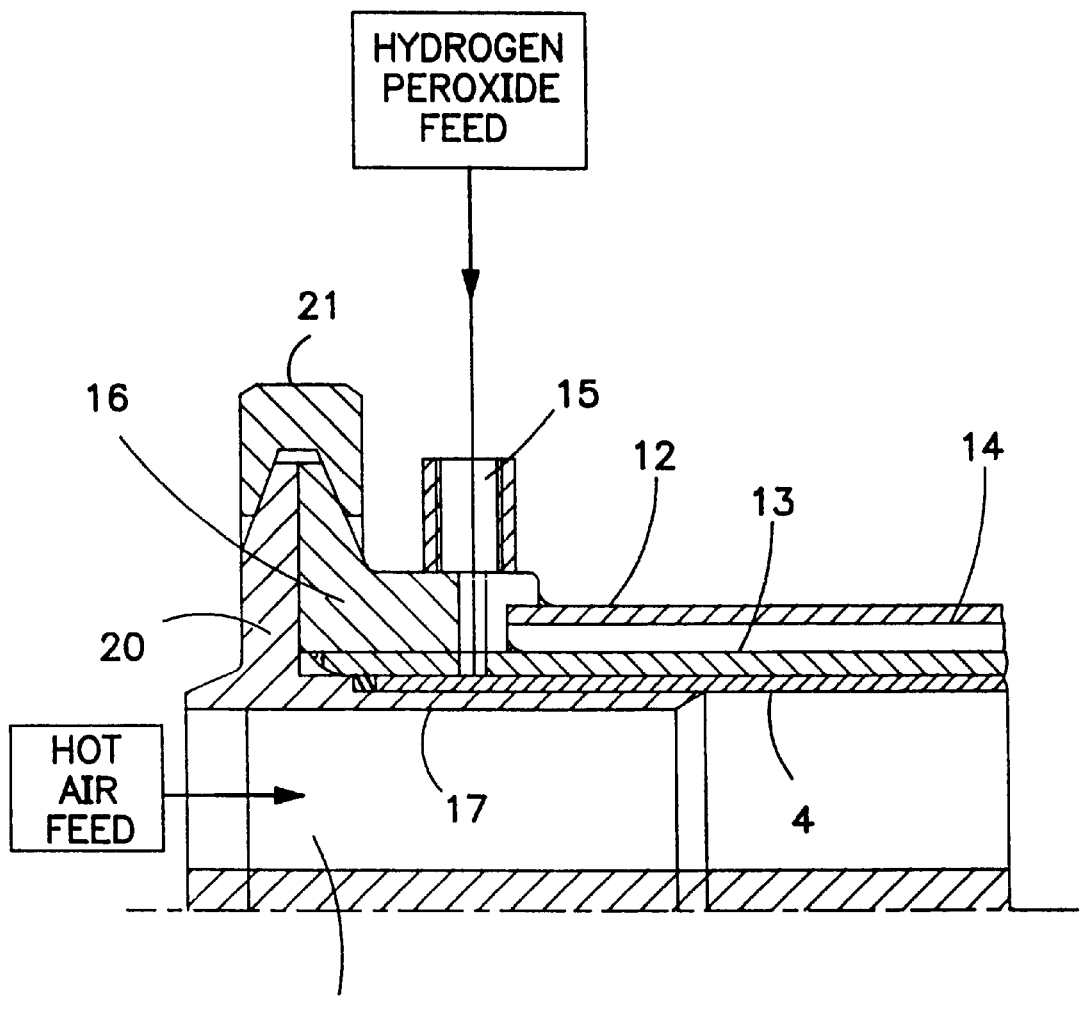
FIG. 2 shows a cross section of a portion of the apparatus of FIG. 1.

In operation and with reference to FIG. 2, the steam jacket (3) of the vaporiser comprises two concentric tubes (12,13) and then which are heated by steam, at a temperature of 120° C., flowing through the channel (14). The liquid hydrogen peroxide, represented in FIG. 2 by a labelled box and arrow, arriving through inlet (15) diffuses through the porous tube (4), where it is totally vaporised by the heating of tube (13), enters the feeding tube (10) and mixes with the arriving hot air stream, represented in FIG. 2 by a labelled box and arrow, fed to and within and longitudinally through the tube (10). The vaporiser comprises further a connecting part (16), which is necessary for allowing said vaporiser to be disposed in the feeding tube (10). A second part (20) comprises an extension (17) for preventing the liquid hydrogen peroxide from directly dripping into the air stream. A connecting ring (21)joins the connecting part (16) with the part (20). Taking in account the presence of the steam jackets (5,11), no condensation occurs, and also with reference to FIG. 1, the mixture of air and hydrogen peroxide flows through the feeding tube (10) at the nozzles (8) to sterilise the containers (9), which are then ready to go to the drying stage (not shown) and finally, under the aseptic filling nozzle. Three seconds are normally necessary for the sterilisation of each container.

In the case of an apparatus operating with several inlets (15), the presence of the extension (17) is no more useful.

EXAMPLE

The apparatus of FIGS. 1–2 is used with hydrogen peroxide at a concentration of 35% and operating with a steam jacket at 120° C. for the sterilisation of containers (volume of 200 ml) for aseptic applications. A concentration of the hydrogen peroxide in the gaseous mixture of 10 mg/liter of air is used.

The nozzle (8) operates at 30 l/min. to reach a decimal reduction of 5 D with *Bac. subtilis*, var. *globigii* and exposure time of 3 sec.

We claim:

1. A process for supplying hydrogen peroxide for sterilizing a surface comprising feeding a stream of hot air to and within and longitudinally through a tube which comprises a porous section and diffusing vaporized hydrogen peroxide from the porous section into the hot air stream to obtain a combined hot air and vaporized hydrogen peroxide stream mixture for supplying the vaporized hydrogen peroxide to a surface for sterilizing the surface.

2. A process according to claim 1 further comprising feeding liquid hydrogen peroxide to the porous section for forming a film on the porous section and heating the porous section to a temperature to vaporize the hydrogen peroxide for diffusion via the porous section into the hot air stream.

3. A process according to claim 2 wherein the porous section is heated to a temperature of from 110° C. to 130° C. for vaporizing the liquid hydrogen peroxide.

4. A process according to claim 2 wherein the porous section is heated to a temperature of around 120° C. for vaporizing the liquid hydrogen peroxide.

5. A process according to claim 1 further comprising monitoring the combined stream mixture and measuring hydrogen peroxide concentration of the mixture.

6. A process according to claim 5 wherein the concentration is measured with a photometer.

7. A process according to claim 5 wherein the concentration is measured with a thermal catalytic decomposition catalyst.

8. A process according to claim 1 to or 2 wherein the porous section has pores having a diameter of from 20 microns to 80 microns.

9. A process according to claim 8 wherein the porous section has a thickness of from 3 mm to 4 mm.

10. A process according to claim 8 wherein the hot air stream is fed to, within and through the tube at a rate of from 20 l/min to 50 l/min and wherein the hydrogen peroxide is diffused so that the combined stream mixture has a hydrogen peroxide concentration of from 5 mg to 20 mg per liter hot air.

11. A process according to claim 10 wherein the porous section has a thickness of from 3 mm to 4 mm.

12. A process according to claim 1 or 2 wherein the porous section is a sintered metal tube.

13. A process according to claim 8, wherein the porous section has a thickness of from 3 mm to 4 mm.

14. A process according to claim 1 or 2 wherein the hydrogen peroxide is diffused so that the combined stream mixture has a hydrogen peroxide concentration of from 5 mg to 20 mg per liter hot air.

15. A process according to claim 14 wherein the hot air stream is fed to, within and through the tube at a rate of from 20 l/min to 50 l/min.

16. A process according to claim 1 or 2 wherein the tube including the porous section is maintained at a temperature on an order of 120° C.

* * * * *

UNITED STATES PATENT AND TRADEMARK OFFICE
CERTIFICATE OF CORRECTION

PATENT NO. : 6, 096, 265
DATED : August 1, 2000
INVENTOR(S) : Urlich MEZGER, et al.

It is certified that error appears in the above-identified patent and that said Letters Patent is hereby corrected as shown below:

On the title page under the heading "U.S. PATENT DOCUMENTS", insert -- 4,863,688, Schmidt, et al., 422/28 --.

Column 3, line 64, after the comma after "peroxide", insert -- represented in Fig. 1 by a labelled box and arrow, --.

Column 3, line 67, after the comma after "stream", insert -- represented in Fig. 1 by a labelled box and arrow, --.

In claim 13, line 1 (col. 6, ln. 5) delete "8" and insert therefor -- 12 --.

Signed and Sealed this

Twenty-fourth Day of April, 2001

Attest:

NICHOLAS P. GODICI

*Attesting Officer*    *Acting Director of the United States Patent and Trademark Office*